(12) United States Patent
Karabelas et al.

(10) Patent No.: US 6,337,342 B1
(45) Date of Patent: Jan. 8, 2002

(54) BIS-ARYL OR HETEROARYL INDOLES

(75) Inventors: Kostas Karabelas; Matti Lepisto; Peter Sjö, all of Lund (SE)

(73) Assignee: AstraZeneca AB (SE)

( * ) Notice: Subject to any disclaimer, the term of this patent is extended or adjusted under 35 U.S.C. 154(b) by 0 days.

(21) Appl. No.: 09/230,710

(22) PCT Filed: Dec. 14, 1998

(86) PCT No.: PCT/SE98/02300

§ 371 Date: Jan. 29, 1999

§ 102(e) Date: Jan. 29, 1999

(87) PCT Pub. No.: WO99/32483

PCT Pub. Date: Jul. 1, 1999

(30) Foreign Application Priority Data

Dec. 23, 1997 (SE) .............................. 9704874
Jul. 13, 1998 (SE) .............................. 9802539

(51) Int. Cl.[7] .................. A61K 31/4152; C07D 403/04

(52) U.S. Cl. .................. 514/392; 548/312.1; 548/311.1

(58) Field of Search .................. 514/392; 548/312.1

(56) References Cited

U.S. PATENT DOCUMENTS

| | | | |
|---|---|---|---|
| 3,642,803 A | 2/1972 | Welstead, Jr. | 260/293.61 |
| 3,821,389 A | 6/1974 | Grivas | 424/270 |
| RE28,973 E | 9/1976 | Welsted, Jr. | 260/293.61 |
| 4,031,221 A | 6/1977 | Helsley et al. | 424/267 |
| 4,062,869 A | 12/1977 | Weston | 260/326.16 |
| 4,466,976 A | 8/1984 | Klose et al. | 424/273 |
| 4,532,250 A | 7/1985 | Stout et al. | 514/341 |
| 4,585,771 A | 4/1986 | Klose et al. | 514/220 |
| 4,598,079 A | 7/1986 | Beyerle et al. | 514/252 |
| 4,912,125 A | 3/1990 | Huebner | 514/402 |
| 5,057,614 A | 10/1991 | Davis et al. | 548/466 |
| 5,077,293 A | 12/1991 | Smith et al. | 514/253 |
| 5,192,770 A | 3/1993 | Clark et al. | 514/305 |
| 5,380,746 A | 1/1995 | Barth et al. | 514/514 |
| 5,399,712 A | 3/1995 | Hill | 578/455 |
| 5,466,699 A | 11/1995 | Robertson et al. | 514/323 |
| 5,516,915 A | 5/1996 | Barth et al. | 548/455 |
| 5,545,636 A | 8/1996 | Heath et al. | 514/214 |
| 5,612,362 A | 3/1997 | Macleod | 514/392 |
| 5,668,152 A | 9/1997 | Heath, Jr. et al. | 514/323 |
| 5,948,907 A | 9/1999 | Faul et al. | 540/469 |
| 6,015,807 A | 1/2000 | Engel et al. | 514/183 |
| 6,054,590 A | 4/2000 | Poindexter et al. | 543/311.1 |
| 6,153,641 A | 11/2000 | Bergstrand et al. | 514/514 |

FOREIGN PATENT DOCUMENTS

| | | |
|---|---|---|
| DE | 3141063 A1 | 4/1983 |
| EP | 0464604 A2 | 1/1992 |
| EP | 0490263 A1 | 6/1992 |
| EP | 0540956 A1 | 11/1993 |
| EP | 0675125 A1 | 10/1995 |
| FR | 7311450 | 3/1973 |
| GB | 1500176 | 2/1978 |
| SU | 389096 | 7/1973 |
| WO | WO 93/18765 | 9/1993 |
| WO | WO 95/17182 | 6/1995 |
| WO | WO 96/01825 | 1/1996 |
| WO | WO 98/13368 | 4/1998 |
| WO | WO 98/43632 | 10/1998 |

OTHER PUBLICATIONS

Pereira et al., "Synthesis and Biological Evaluation of Monoindolyl and Indolocarbazolyl Oxazolones and Imidazolones", Chem. Pharm. Bull. 45(4): 733–736 (1997).
Abstract of JP 2–188579 A, Patent Abstracts of Japan, vol. 14, No. 459, C–767, 1990.
Pereira et al. J. Antibiot.,49, 380–385 (1996).
Bergstrand et al., "Modulation of Neutrophil Superoxide Generation by Inhibitors of Protein Kinase C, . . . " The Journal of Pharmacology and Experimental Therapeutics, vol. 263, No. 3, pp. 1334–1346 1992.
Chakravarthy et al., "The Direct Measurement of Protein Kinase C (PKC) Activity in Isolated Membranes Using a Selective Substrate", Analytical Biochemistry, 1991, vol. 196, pp. 144–150.
Gazit et al., "Tyrphostins. 5. Potent Inhibitors of Platelet–Derived Growth Factor Receptor TyrosineKinase: Structure–Activity Relationships . . . ", J. Med. Chem., 1996, vol. 39, pp. 2170–2177.

(List continued on next page.)

Primary Examiner—Floyd D. Higel
Assistant Examiner—Kamal Saeed
(74) Attorney, Agent, or Firm—Fish & Richardson, P.C.

(57) ABSTRACT

The present invention relates to compounds of formula (I):

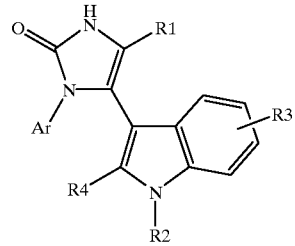

(I)

wherein:

Ar is an optionally substituted aromatic or heteroaromatic group,

R1 is H, $C_{1-6}$alkyl, $CF_3$, phenyl, benzyl, carbo$C_{1-6}$alkoxy, carbamoyl, or methyl(N—$C_{1-6}$alkylcarbamoyl)

R2 is H, $C_{1-6}$alkyl, amino$C_{1-6}$alkyl, hydroxy$C_{1-6}$alkyl, (mono- or di- $C_{1-6}$alkyl)amino$C_{1-6}$alkyl, (amino$C_{1-3}$alkylphenyl)$C_{1-3}$alkyl, amidinothio $C_{1-6}$alkyl, R3 is H or $C_{1-6}$alkoxy, R4 is H or together with R2, forms an annulated ring which may be substituted by hydroxy$C_{1-3}$alkyl or amidinothio $C_{1-3}$alkyl, or amino$C_{1-3}$alkyl;

and pharmaceutically acceptable salts thereof;
and the use of such compounds in medical therapies.

12 Claims, No Drawings

OTHER PUBLICATIONS

Granet et al., "A Microtiter Plate Assay for Protein Kinase $C^1$", Analytical Biochemistry, 1987, 163:458–463.

Olsson et al., "Activation of Human Neutrophil Protein Kinase C in vitro by 1, 2–isopropylidene–3–decanoyl–sn–glcerol (Ip ($COC_9$), Cellular Signaling, 1989 1(4) :405–410.

Galzunov et al., "Investigation of the Riboflavine Operon of Bacillus Subtilis V11. Bicochemical Study of Mutants Relating to Early Stages of Biosythesis" Translated from Genetika 10(11):83–92, 1974, see Chemical Abstracts vol. 82 No. 13 (1975) abstract 82817b.

Elisabete R. Pereira et al., "Synthesis and Biological Evaluation of Monoindolyl and Indolocarbazolyl Oxazolones and Imidazolones", Chem. Pharm. Bull. 45(4) 733–736, Pharmaceutical Study Of Japan: 1997.

Patent Abstracts of Japan: vol. 14 No. 459 (C–767) (4402); Oct. 4, 1990.

Yuji Oikawa et al., "Synthesis of Pimprinine And Related Oxazolylindole Alakaloids From N–ACYL Derivatives Of Tryptamine And Methyl Ester By DDQ Oxidation", Heterocycles. vol.12. No.11, 1979.

Carmen Galvez et al., "A Conveinent Preparation of Haloaminobenzo[b]thiophene Derivatives", Communications (932–933); Nov. 1983.

Thomas W. von Geldern et al., "Azole Endothelin Antagonists. 1. A Receptor Model Explains an Unusual Structure–Activity Profile", J. Med. Chem. 1996, 39, 957–967.

J. Bergman et al., "Synthesis And Reactions Of Some 3–(2–Haloacyl) indoles",Tetrahedron. vol. 29, pp. 971–976; Pergamon Press 1973.

Elisabete R. Pereira et al., "Synthesis And Antimicrobial Activities of Five–membered Ring Heterocycles Coupled to Indole Moietics", The Journal of Antibiotics. Apr. 1996; vol. 49 No.4 pp. 380–385.

BIS-ARYL OR HETEROARYL INDOLES

This application is a 371 of PCT/SE98/02300 filed Dec. 14, 1998.

The present invention relates to novel compounds which are protein kinase C inhibitors, methods for their preparation, intermediates therefor and pharmaceutical compositions comprising them.

Protein kinase C (PKC) is a family of phospholipid-dependent serine/threonine-specific protein kinases which play an important role in cellular growth control, regulation and differentiation.

Since the activation of PKC has been implicated in several human disease processes, including various forms of cancer, different forms of inflammatory and/or immunological disorders as well as some neurological disorders, inhibition of PKC could be of therapeutic value in treating these conditions.

Several classes of compounds have been identified as PKC inhibitors, e.g. isoquinoline sulphonamides, sphingosine and related sphingolipids, indolocarbazoles and bisindolylmaleimides.

EP 0 328 026 describes the use of certain bisindolylmaleimides, a class of compounds related to the indolocarbazoles, in medicaments for the treatment of various conditions.

Baskakow et al.; SU 389096; 1973 describes 1,5 substituted diphenyl imidazolones although these are not suggested to be of any therapeutic potential.

Although PKC inhibitors are described in the prior art, there is a need for specific anti-inflammatory and immunosuppressive compounds which are suitable for oral administration, and for inhalation.

The present invention provides kinase inhibitors which are particularly PKC inhibitors, methods for their preparation and intermediates used for their preparation.

The present invention also provides the use of the compounds of the present invention for the treatment of inflammatory, immunological, bronchopulmonary, cardiovascular, oncological or CNS-degenerative disorders.

Also provided by the present invention are pharmaceutical compositions comprising a compound according to the present invention, as active ingredient, together with a pharmaceutically acceptable adjuvant, diluent or carrier.

The present invention provides compounds of formula (I)

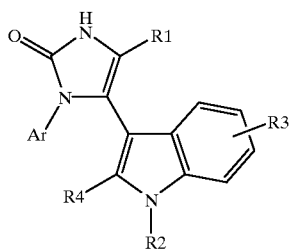

(I)

wherein:
Ar is an optionally substituted aromatic or heteroaromatic group,
R1 is H, $C_{1-6}$alkyl, fluoro substituted $C_{1-6}$alkyl, phenyl, benzyl, carbo$C_{1-6}$alkoxy, carbamoyl, or methyl(N—$C_{1-6}$alkylcarbamoyl),
R2 is H, $C_{1-6}$alkyl, amino$C_{1-6}$alkyl, hydroxy$C_{1-6}$alkyl, (mono- or di- $C_{1-6}$alkyl)amino$C_{1-6}$alkyl, (amino$C_{1-3}$alkylphenyl)$C_{1-3}$alkyl, or amidinothio $C_{1-6}$alkyl, R3 is H or $C_{1-6}$alkoxy,
R4 is H or together with R2, forms an annulated ring which may be substituted by hydroxy$C_{1-3}$alkyl or amidinothio $C_{1-3}$alkyl, or amino$C_{1-3}$alkyl,
and pharmaceutically acceptable salts thereof.

For compounds of formula (I), the following independent preferences apply:
Ar is an optionally substituted bicyclic aromatic or an optionally substituted bicyclic heteroaromatic group,
R1 is H or methyl; or if a fluoro substituted $C_{1-6}$ alkyl, is preferably $CF_3$, when R4 is H, R2 is H, methyl, aminopropyl, hydroxypropyl or amidinothiopropyl, when R2 and R4 together form an annulated ring, they together comprise 4 or 5 carbons,
R3 is H or methoxy.

In more preferred embodiments of formula (I), Ar comprises a single heteroatom selected from N, O and S.

In yet more preferred embodiments of formula (I), Ar is selected from benzothiophene, naphthyl, phenoxyphenyl, or an optionally substituted indolyl which if substituted is preferably substituted with aminobutyl, aminomethyl benzyl, ethoxy carbamate, or 2,2,2-trichloroethylcarbamate.

Preferred compounds according to the present invention include:

5-[1-(3-Aminopropyl)-3-indolyl]-1-(3-indolyl)-1,3-dihydroimidazol-2-one,

5-[1-(3-Aminopropyl)-3-indolyl]-1-(3-benzo[b]thoiphenyl-1,3-dihydroimidazol-2-one, 5-[1-(3-Aminopropyl)-3-indolyl]-1-(1-naphthyl)-1,3-dihydroimidazol-2-one, 5-[1-{3-(Aminomethyl)benzyl}-3-indolyl]-1-(3-indolyl)-1,3-dihydroimidazol-2-one, 5-[1-(3-Aminopropyl)-3-indolyl]-1-(3-indolyl)-4-methyl-1,3-dihydroimidazol-2-one, 5-[1-(3-Amidinothiopropyl)-3-indolyl]-1-(3-indolyl)-1,3-dihydroimidazol-2-one, 5-{1-[3-(N,N-Dimethylamino)propyl]-3-indolyl}-1-(3-indolyl)-1,3-dihydroimidazol-2-one; and 5-[1-(3-Aminopropyl)-3-indolyl]-1-(3-indolyl)-4-phenyl-1,3-dihydroimidazol-2-one;

and salts thereof.

Salts of the compounds of formula (I) according to the invention are preferably pharmaceutically acceptable salts. Other salts may however be useful in the preparation of the compounds or in the preparation of pharmaceutically acceptable salts.

Pharmaceutically acceptable salts of compounds of the present invention are preferably those well known in the art as being suitable and are preferably acid addition salts and more preferably acetate salts or trifluoroacetate salts.

Compounds of formula (I) may be synthesised in the following ways:

(A) Compounds of formula (I) may be synthesised by converting a compound of formula (I) to a pharmaceutically acceptable salt thereof, or vice versa; or converting a pharmaceutically acceptable salt of a compound of formula (I) into a different pharmaceutically acceptable salt.

(B) Compounds of formula (I) may be synthesised by intramolecular condensation of a compound of formula (III):

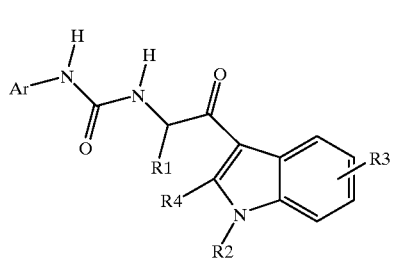

(III)

in which Ar, R1, R2, R3 and R4 are as defined for formula (I).

The condensation may be performed under acidic conditions (preferably acetic acid or scandium(III) trifluoromethanesufonate) at elevated temperatures (preferably 110° C.).

Compounds of formula (I) in which Ar carries functional groups which might be sensitive to or interfere with the reaction conditions in process (B), can be prepared by intramolecular condensation of a corresponding compound of formula (III), but in which the functional groups on Ar are suitably protected, followed by subsequent deprotection.

Functional groups that might be sensitive for or interfere with the reaction conditions in process (B), as well as suitable protecting groups and deprotecting methods, are evident to those skilled in the art.

Compounds of formula (I), in which at least one of $R_2$ or Ar carries an amino, or hydroxy group; and pharmaceutically acceptable salts thereof, may be prepared by deprotecting a compound of formula (II) corresponding to formula (I) but in which at least one of $R_2$ or Ar carries a protected amino or hydroxy group.

In the processes described above, the protecting groups and conditions for deprotection are well known to those skilled in the art. Suitable protecting groups for amino groups are e.g phthaloyl groups and the deprotecting agent may be methylamine in e.g. water. The deprotecting step may be carried out in a suitable solvent, e.g tetrahydrofuran at about 10–30° C., e.g for about 5 hours. The hydroxy groups may be protected as their corresponding acetoxy groups and the deprotecting agent may be methylamine in e.g. water. The deprotecting step may be carried out in a suitable solvent, e.g tetrahydrofuran at about 10–30° C., e.g for about 16 hours.

The starting materials for the above processes (A) and (B) may be made by the methods described herein and particularly by those methods set out in the Examples or by methods analogous thereto. Other conventional methods for making the starting materials will be evident to those skilled in the art.

Compounds of formula (III) in which R2 is not H may be synthesised by alkylation with an optionally substituted alkylating agent, of compounds of formula (IV). The alkylating agent may be an alkyl halide, or an alkyl halide carrying a dialkyl amino group, or an alkylating agent carrying a protected amino or hydroxy group.

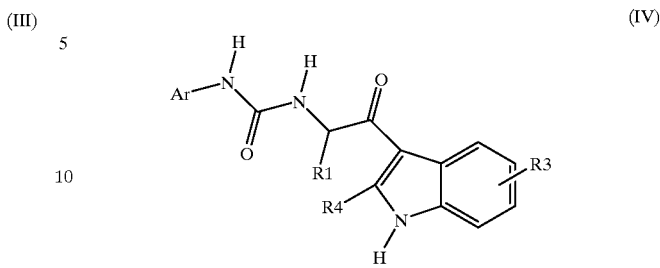

(IV)

in which Ar, R1, R3 and R4 are as defined for formula (I).

Compounds of formula (III), in which R2 is not H, and Ar, R1, R3 and R4 are as defined in formula (I), may also be prepared by reaction of the appropriate isocyanate with a relevant alpha-ketoamine carrying R2, and in which R2 is not H, by standard techniques.

Compounds of formula (IV) may be prepared by reaction of the appropriate isocyanate with a relevant alpha-ketoamine by standard techniques.

Compounds of formula (I) in which R2 is alkyl and Ar is an indole, substituted on the indole nitrogen with an alkyl carrying an amino or hydroxy group, may be prepared by deprotecting a compound of formula (V) in which R5 is an alkyl carrying a protected amino or hydroxy group.

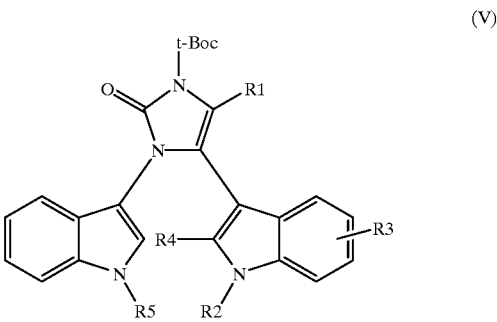

(V)

in which R1, R2, R3, and R4 are as defined for formula (I).

The protecting groups and conditions for the deprotection are the same as mentioned earlier.

Compounds of formula (V) may be prepared by selective removal of a Troc group from a compound of formula (VI)

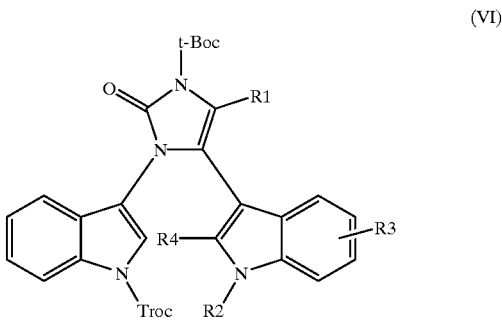

(VI)

in which R1, R2, R3 and R4 are as defined for formula (I), followed by subsequent alkylation under standard conditions, with an alkyl carrying a protected amino or hydroxy group. Selective deprotection of the Troc group is carried out with cadmium in acetic acid and DMF.

Compounds of formula (VI) may be prepared by introducing a Boc group, under standard conditions, to a compound of (I) but in which the Ar group is a Troc protected indole. Such a compound is prepared from a compound of formula (III), but in which the Ar group is a Troc protected indole.

Also provided according to the present invention are compounds of the present invention for use in medical therapy; the use of compounds of the present invention in the manufacture of medicaments for use in the treatment of the conditions described herein; and methods of medical therapy comprising the administration of an effective amount of a compound of the present invention to an individual requiring such therapy.

Novel intermediates as described herein and their use in the manufacture of other compounds of the present invention also form part of the invention.

The compounds of formula (I), and pharmaceutically acceptable salts thereof, are useful because they demonstrate pharmacological activity. In particular they demonstrate activity as kinase inhibitors, especially PKC inhibitors, e.g. as is shown by their activity in the in vitro assays described in Granet, R. A. et al, Analyt. Biochem. 1987; 163, 458–463; Olsson, H. et al, Cell Signal 1989, 1, 405–410; and Chakravarthy, B. R. et al, Analyt. Biochem. 1991, 196, 144–150.

The compounds of the invention are indicated for use in the treatment of inflammatory, immunological, bronchopulmonary, cardiovascular, oncological or CNS-degenerative disorders; preferably for oral or topical treatment of inflammatory and/or immunological disorders, such as the oral or topical treatment of airway diseases involving inflammatory conditions, e.g. asthma, bronchitis; or atopic diseases, e.g. rhinitis or atopic dermatitis; inflammatory bowel diseases, e.g. Crohn's disease or colitis; autoimmune diseases e.g. multiple sclerosis, diabetes, atherosclerosis, psoriasis, systemic lupus erythematosus or rheumatoid arthritis; malignant diseases, e.g. skin or lung cancer; HIV infections or AIDS; or for inhibiting rejection of organs/transplants.

The dose of the compound to be administered will depend on the relevant indication, the age, weight and sex of the patient and may be determined by a physician. The dosage will preferably be in the range of from 0.1 mg/kg to 100 mg/kg.

The compounds may be administered topically, e.g. to the lung and/or the airways, in the form of solutions, suspensions, HFA aerosols or dry powder formulations, e.g. formulations in the inhaler device known as the Turbuhaler®; or systemically, e.g. by oral administration in the form of tablets, pills, capsules, syrups, powders or granules, or by parenteral administration, e.g. in the form of sterile parenteral solutions or suspensions, or by rectal administration, e.g. in the form of suppositories.

The compounds of the invention may be administered on their own or as a pharmaceutical composition comprising the compound of the invention in combination with a pharmaceutically acceptable diluent, adjuvant or carrier. Particularly preferred are compositions not containing material capable of causing an adverse, e.g. an allergic, reaction.

Dry powder formulations and pressurized HFA aerosols of the compounds of the invention may be administered by oral or nasal inhalation. For inhalation the compound is desirably finely divided. The finely divided compound preferably has a mass median diameter of less than 10 gm, and may be suspended in a propellant mixture with the assistance of a dispersant, such as a $C_8$–$C_{20}$ fatty acid or salt thereof, (e.g. oleic acid), a bile salt, a phospholipid, an alkyl saccharide, a perfluorinated or polyethoxylated surfactant, or other pharmaceutically acceptable dispersant.

The compounds of the invention may also be administered by means of a dry powder inhaler. The inhaler may be a single or a multi dose inhaler, and may be a breath actuated dry powder inhaler.

One possibility is to mix the finely divided compound with a carrier substance, e.g. a mono-, di- or polysaccharide, a sugar alcohol, or an other polyol. Suitable carriers are sugars, e.g. lactose, glucose, raffinose, melezitose, lactitol, maltitol, trehalose, sucrose, mannitol; and starch. Alternatively the finely divided compound may be coated by another substance. The powder mixture may also be dispensed into hard gelatine capsules, each containing the desired dose of the active compound.

Another possibility is to process the finely divided powder into spheres which break up during the inhalation procedure. This spheronized powder may be filled into the drug reservoir of a multidose inhaler, e.g. that known as the Turbuhaler® in which a dosing unit meters the desired dose which is then inhaled by the patient. With this system the active compound, with or without a carrier substance, is delivered to the patient.

For oral administration the active compound may be admixed with an adjuvant or a carrier, e.g. lactose, saccharose, sorbitol, mannitol; a starch, e.g. potato starch, corn starch or amylopectin; a cellulose derivative; a binder, e.g. gelatine or polyvinylpyrrolidone, and/or a lubricant, e.g. magnesium stearate, calcium stearate, polyethylene glycol, a wax, paraffin, and the like, and then compressed into tablets. If coated tablets are required, the cores, prepared as described above, may be coated with a concentrated sugar solution which may contain e.g. gum arabic, gelatine, talcum, titanium dioxide, and the like. Alternatively, the tablet may be coated with a suitable polymer dissolved in a readily volatile organic solvent.

For the preparation of soft gelatine capsules, the compound may be admixed with e.g. a vegetable oil or polyethylene glycol. Hard gelatine capsules may contain granules of the compound using either the above mentioned excipients for tablets. Also liquid or semisolid formulations of the drug may be filled into hard gelatine capsules.

Liquid preparations for oral application may be in the form of syrups or suspensions, for example solutions containing the compound, the balance being sugar and a mixture of ethanol, water, glycerol and propylene glycol. Optionally such liquid preparations may contain colouring agents, flavouring agents, saccharine and/or carboxymethylcellulose as a thickening agent or other excipients known to those skilled in art.

The compounds of the invention may also be administered in conjunction with other compounds used for the treatment of the above conditions.

The term 'medical therapy' as used herein is intended to include prophylactic, diagnostic and therapeutic regimens carried out in vivo or ex vivo on humans or other mammals.

Compounds of the present invention include all stereoisomers, pure and mixed racemates, and mixtures thereof.

The following Examples illustrate, but in no way limit the invention.

General Methods

All reactions were performed in dried glassware in an argon atmosphere at room temperature, unless otherwise noted. THF was distilled from sodium benzophenone ketyl under $N_2$ prior to use. N,N-dimethyl formamide was distilled from calcium hydride and stored over molecular sieves. All other solvents and reagents and solvents were used as received.

Chromatography, unless otherwise stated, was carried out using a Chromatotron® (a centrifugally accelerated, radial preparative chromatograph), the plates used were prepared using Merck Silica Gel PF$_{254}$ containing gypsum.

$^1$H-NMR spectra were recorded on a Varian Inova-400 or Unity-500+ instrument. The central solvent peak of chloroform-d ($\delta_H$ 7.27 ppm), dimethylsulfoxide-d$_6$ ($\delta_H$ 2.50 ppm) or methanol-d$_4$ ($\delta_H$ 3.35 ppm) were used as internal references. Low-resolution mass spectra were recorded on an Autospec-Q, Fisons Analytical, double focusing sector instrument equipped with a LSIMS interface. Low resolution mass spectra were also obtained on a Hewlett Packard 1100 LC-MS system equipped with an APCI ionisation chamber.

3-(Azidocarbonyl)-1-(2,2,2-trichloroethoxycarbonyl) indole was prepared in 52% yield following the procedure outlined by Suvorov et al. Khimiya Gereotsiklicheskikh Soedinenii, 8 (1975) 1099–1105.

$^1$H-NMR (400 MHz, DMSO-d$_6$): δ 5.27 (2H, s), 7.43 (1H, t, J 7.4 Hz), 7.49 (1H, t, J 7.6 Hz), 8.12 (1H, d, J 7.8 Hz), 8.16 (1H, d, J 8.0Hz), 8.26 (1H, s).

EXAMPLE 1

1-(3-Indolyl)-5-(1-methyl-3-indolyl)-1,3-dihydroimidazol-2-one a) 3-{3-[2-(3-Indolyl)-2-oxoethyl]ureido}-1-(ethoxycarbonyl)indole A solution of 3-(azidocarbonyl)-1-(ethoxycarbonyl) indole Suvorov (ibid) (1.32 g, 5.12 mmol) in benzene (25 ml) was heated to reflux for 7 hours. After cooling to room temperature, THF (25 ml) and [2-(3-indolyl)-2-oxoethyl] ammonium bromide [Oikawa,Y. et al. Heterocycles 12 (1979) 1457–1462] (1.31 g, 5.12 mmol) were added immediately followed by ethyldiisopropylamine (0.89 ml, 5.12 mmol). After stirring for 1.5 hours the formed precipitate was removed by filtration and washed with THF followed by water. The sub-title compound (1.65 g, 79%) was obtained as a white solid after drying.

$^1$H-NMR (500 MHz, DMSO-d$_6$): δ 1.38 (3H, t, J 7.3 Hz), 4.41 (2H, q, J 7.3 Hz), 4.60 (2H, d, J 5.0 Hz), 6.71 (1H, t, J 5.0 Hz), 7.18–7.27 (2H, m), 7.33 (1H, t, J 7.7 Hz), 7.39 (1H, t, J 7.7Hz), 7.50 (1H, d,J 6.6 Hz), 7.72 (1H, d, J 7.5 Hz), 7.83 (1H, s), 8.11 (1H, d, J 8.2 Hz,), 8.19 (1H, d, J 6.7 Hz), 8.47 (1H, d, J 3.1 Hz), 9.12 (1H, s), 12.05 (1H, br s, indole NH)

FAB-MS: m/z 429 [MNa+], 405 [MH+].

b) 3-{3-[2-(1-Methyl-3-indolyl)-2-oxoethyl]ureido}-1-(ethoxy-carbonyl)indole

The product of step a) (1.50 g, 3.71 mmol) and K$_2$CO$_3$ (2.05 g, 14.8 mmol) was mixed in dry DMF (25 ml). Methyl iodide (0.25 ml, 4.08 mmol) was added and the reaction allowed to proceed until HPLC showed that the starting material had been consumed, generally about 3 hours. Aqueous acetic acid (1M, 50 ml) and ethyl acetate (50 ml) were added and the phases separated whereupon the sub-title product precipitated. The organic phase containing the precipitate was washed with water (2×25 ml), filtered off and washed with water to give the sub-title product (0.96 g, 62%) as a white solid after drying.

$^1$H-NMR (500 MHz, DMSO-d$_6$): δ 1.37 (3H, t, J 7.2 Hz), 3.90 (3H, s), 4.41 (2H, q, J 7.1 Hz), 4.57 (2H, d, J 5.2 Hz), 6.73 (1H, br t, J 5.0 Hz), 7.26 (1H, t, J 7.2 Hz), 7.28–7.34 (3H, m), 7.39 (1H, t, J 7.6 Hz), 7.57 (1H, d, J 7.9 Hz), 7.72 (1H, d, J 7.9 Hz), 7.82 (1H, s), 8.10 (1H, br d, J 8.6 Hz), 8.19 (1H, d, J 7.8 Hz), 8.50 (1H, s), 9.13 (1H, s).

c) 1-[1-(Ethoxycarbonyl)-3-indolyl]-5-(1-methyl-3-indolyl)-1,3-dihydroimidazol-2-one The product of step b) (2.63 g, 6.29 mmol) was suspended in acetic acid (30.0 ml) and heated to 110° C. until all the starting material has been consumed, i.e. about 3 hours. The solvent was removed and the residue titurated with diethyl ether to give the sub-title compound (1.84 g, 74%) as an off-white solid.

$^1$H-NMR (400 MHz, DMSO-d$_6$): δ 1.38 (3H, t, J 7.0 Hz), 3.57 (3H, s), 4.44 (2H, q, J 7.0 Hz), 6.77 (1H, br d, J 2.1 Hz), 6.94 (1H, s), 7.00 (1H, t, J 7.3 Hz), 7.10–7.17 (2H, m), 7.21 (1H, d, J 7.6 Hz), 7.30–7.36 (2H, m), 7.57 (1H, d, J 8.0 Hz), 7.78 (1H, s), 8.09 (1H, d, J 8.1 Hz), 10.44 (1H, s).

FAB-MS: 401 [MH+], 801 [MH2+].

d) The sub-title product of step c) (0.17 g, 0.44 mmol) was dissolved in THF (3 ml) and aqueous methyl amine (40%, 3 ml) and stirred for 30 minutes. The solvent was removed and the product precipitated from diethyl ether to give the title compound (0.14 g, 94%) as a slightly brown solid.

$^1$H-NMR (400 MHz, DMSO-d$_6$): δ 3.53 (3H, s), 6.68 (1H, s), 6.71 (1H, s), 6.93 (1H, t, J 7.6 Hz), 6.98 (1H, t, J 7.6 Hz), 7.08 (1H, t, J 7.0Hz), 7.11 (1H, t, J 7.0 Hz), 7.18 (1H, d, J 7.8 Hz), 7.32 (1H, d, J 8.1 Hz), 7.35–7.39 (2H, m), 7.56 (1H, d, J 7.9 Hz), 10.24 (1H, s), 11.17 (1H, br s).

FAB-MS: m/z 329 [MH+], 657 [MH2+].

EXAMPLE 2

1,5-Bis-(3-indolyl)-1,3-dihydroimidazol-2-one a) 1-(1-Ethoxycarbonyl-3-indolyl)-5-(3-indolyl)-1,3-dihydroimidazol-2-one The product of Example 1 a) (0.90 g, 2.23 mmol) was suspended in acetic acid (20.0 ml) and heated to 110° C. until all the starting material has been consumed i.e. about 3.5 hours. The solvent was removed and the residue chromatographed, eluting with CH$_2$Cl$_2$—MeOH (100:10) to give the title compound (0.69 g, 80%) obtained as an off-white solid.

$^1$H-NMR (500 MHz, DMSO-d$_6$): δ 1.37 (3H, t, J 7.1 Hz), 4.44 (2H, q, J 7.1 Hz), 6.80 (1H, d, J 2.4 Hz), 6.82 (1H, d, J 2.6 Hz), 6.99 (1H, t, J 7.6 Hz), 7.07 (1H, t, J 7.6 Hz), 7.14 (1H, t, J 7.4 Hz), 7.19 (1H, d, J 7.8 Hz), 7.29 (1H, d, J 7.9 Hz), 7.32 (1H, d, J 7.7 Hz), 7.60 (1H, d, J 7.9 Hz), 7.80 (1H, s), 8.10 (1H, d, J 8.4Hz), 10.42 (1H, br d, J 2.2 Hz), 10.94 (1H, br s).

FAB-MS: m/z 387 [MH+].

The product of step a (0.055 g, 0.143 mmol) was dissolved in THF (1 ml) and aqueous methylamine (40%, 1 ml). The reaction was complete after 1 hour, solvent removal followed by chromatography on silica eluting with dichloromethane-methanol (100:10), gave the title compound (0.028 g, 63%) as a slightly brown solid.

$^1$H-NMR (400 MHz, DMSO-d$_6$): δ 6.53 (1H, d, J 2.7 Hz), 6.76 (1H, d, J 2.5 Hz), 6.93 (1H, t, J 7.3 Hz), 6.98 (1H, t, J 7.2 Hz), 7.06 (1H, t, J 7.6 Hz), 7.09 (1H, t, J 7.7 Hz), 7.17 (1H, d, J 8.1 Hz), 7.26 (1H, d, J 7.3 Hz), 7.39 (1H, d, J 8.3 Hz), 7.41 (1H, d, J 2.9 Hz), 7.62 (1H, d, J 7.9 Hz), 10.23 (1H, br d, J 2.1 Hz), 10.86 (1H, br s), 11.23 (1H, br s).

FAB-MS: m/z 315 [MH+].

EXAMPLE 3

1-[1-(4-Aminobutyl)-3-indolyl]-5-(1-methyl-3-indolyl)-1,3-dihydroimidazol-2-one trifluoroacetic acid salt a) 3-{3-[2-(3-Indolyl)-2-oxoethyl]ureido}-1-(2,2,2-trichloroethoxycarbonyl)indole The sub-title product was prepared in 71% yield as a white solid following the procedure of Example 1 a) starting from 3-(azidocarbonyl)-1-(2,2,2-trichloroethoxycarbonyl) indole.

¹H-NMR (400 MHz, DMSO-d₆): δ 4.58 (2H, d, J 5.2 Hz), 5.18 (2H, s), 6.70 (1H, t, J 5.0 Hz), 7.14–7.21 (2H, m), 7.34 (1H, t, J 7.4 Hz), 7.39 (1H, t, J 8.1 Hz), 7.43–7.48 (1H, m), 7.72 (1H, d, J 7.6 Hz), 7.89 (1H, s), 8.09–8.17 (2H, m), 8.43 (1H, br d, J 2.6 Hz), 9.19 (1H, s), 12.01 (1H, br s, indole N H).

b) 3-{3-[2-(1-Methyl-3-indolyl)-2-oxoethyl]ureido}-1-(2,2,2-trichloroethoxycarbonyl)indole The sub-title compound, obtained as a white solid, was prepared in 63% yield following the procedure of Example 1 b) starting from the product of step a).

¹H-NMR (400 MHz, DMSO-d₆): δ 3.89 (3H, s), 4.59 (2H, d, J 5.0 Hz), 5.23 (2H, s), 6.84 (1H, t, J 5.0Hz, NH), 7.26 (1H, t, J 7.2 Hz), 7.33 (1H, t, J 6.9 Hz), 7.39 (1H, t, J 7.1 Hz), 7.44 (1H, t, J 7.7 Hz), 7.57 (1H, d, J 8.1 Hz), 7.79 (1H, d, J 7.6 Hz), 7.93 (1H, s), 8.16 (1H, d, J 8.2Hz), 8.20 (1H, d, J 7.7 Hz), 8.51 (1H, s), 9.30 (1H, s).

c) 5-(1-Methyl-3-indolyl)-1-[1-(2,2,2-trichloroethoxycarbonyl)-3-indolyl]-1,3-dihydroimidazol-2-one The sub-title product, obtained as a off-white solid, was prepared in 86% yield following the procedure in Example 1 c) starting from the product of step b). The product was precipitated from diethyl ether.

¹H-NMR (400 MHz, DMSO-d₆): δ 3.60 (3H, s), 5.24 (2H, s), 6.77 (1H, s), 6.97 (1H, t, J 7.8 Hz), 7.03 (1H, s), 7.11 (1H, t, J 7.8 Hz), 7.21 (1H, t, J 7.4 Hz), 7.30–7.41 (3H, m), 7.49 (1H, d, J 8.0 Hz), 7.70 (1H, s), 8.13 (1H, d, J 8.3 Hz), 10.48 (1H, s).

FAB-MS: m/z 503 [MH+].

d) 1-(tert-Butoxycarbonyl)-4-(1-methyl-3-indolyl)-3-[1-(2,2,2-trichloroethoxycarbonyl)-3-indolyl]-1,3-dihydroimidazol-2-one The product of step c) (0.10 g, 0.20 mmol), di-tert-butyl dicarbonate (0.054 g, 0.25 mmol) and a catalytic amount of 4-N,N-dimethylaminopyridine in dry THF (3 ml) was stirred for 5 minutes at room temperature. Removal of the solvent and chromatographic purification on silica, eluting with heptane—ethyl acetate (60:40), gave the sub-title product (0.11 g, 94%) as a slightly brown solid.

¹H-NMR (500 MHz, CDCl₃): δ 1.66 (9H, s), 3.59 (3H, s), 5.01 (2H, s), 6.66 (1H, s), 7.04 (1H, s), 7.16 (1H, dt, J 2.5, 6.0 Hz), 7.21 (1H, t, J 7.6 Hz), 7.25–7.27 (2H, m), 7.33–7.42 (2H, m), 7.67 (1H, d, J 7.9 Hz), 7.71 (1H, s), 8.23 (1H, br d, J 8.2 Hz).

FAB-MS: m/z 602 [MH+], 625 [MNa+].

e) 1-(tert-Butoxycarbonyl)-4-(1-methyl-3-indolyl)-3-(3-indolyl)-1,3-dihydroimidazol-2-one The product of step d) (0.21 g, 0.34 mmol), zink powder (0.23 g, 3.44 mmol) and cadmium(II)chloride (0.020 g, 0.086 mmol) was suspended in DMF (4 ml) and acetic acid (4 ml). The suspesion was stirred for 1 hour at room temperature, ethyl acetate (10 ml) and water (20 ml) were added and the phases separated. The organic phase was washed with water (3×5 ml), dried over Na₂SO₄, solvent removal followed by chromatographic purification on silica, eluting with ethyl acetate, gave the sub-title product (0.12 g, 81%) as a colourless solid.

¹H-NMR (500 MHz, CDCl₃): δ 1.69 (9H, s), 3.40 (3H, s), 6.32 (1H, s), 6.84 (1H, br t, J 2.3 Hz), 6.92–7.00 (2H, m), 7.04–7.09 (2H, m), 7.16–7.26 (3H, m), 7.29–7.33 (1H, m), 7.75 (1H, dt, J 1.4, 2.3 Hz), 9.43 (1H, s).

FAB-MS: m/z 428 [MH+], 451 [MNa+].

f) 1-(tert-Butoxycarbonyl)-3-{1-[4-(1,3-Dioxo-1,3-dihydro-isoindol-2-yl)-butyl]-3-indolyl}-4-(1-methyl-3-indolyl)-2,3-dihydroimidazole-2-one The product of step e) (0.034 g, 0.080 mmol), N-(4-bromobutyl)phthalimide (0.028 g, 0.10 mmol) and sodium hydride (95%, 0.0024 g, 0.10 mmol) was dissolved in dry DMF (0.5 ml). After stirring at room temperature for 1.5 hour HPLC shows complete reaction. The reaction was quenched by addition of aqueous acetic acid (1 M, 2 ml) and ethyl acetate (2 ml), the phases were separated and the organic phase washed with water (1×2 ml). Solvent removal followed by chromatographic purification on silica, eluting with heptane—ethyl acetate (20:80), furnishes the sub-title product (0.019 g, 38%) as a slightly brown solid.

¹H-NMR (500 MHz, CDCl₃): δ 1.61 (9H, s), 1.64–1.79 (4H, m), 3.56 (3H, s), 3.67 (2H, t, J 6.5 Hz), 3.71 (2H, t, J 6.7 Hz), 6.87 (1H, s), 6.97 (1H, s), 7.02 (1H, t, J 7.6 Hz), 7.10–7.18 (2H, m), 7.31 (1H, t, J 7.1 Hz), 7.35 (1H, d, J 8.2 Hz), 7.60 (1H, d, J 8.1 Hz), 7.77 (1H, s), 7.80–7.88 (4H, m), 8.06 (1H, d, J 8.3 Hz).

FAB-MS: m/z 629 [MH+].

The product of step f) (0.018 g, 0.029 mmol) was dissolved in THF (0.25 ml) and aqueous methyl amine (40%, 0.25 ml) and stirred for 1 hour, HPLC shows complete deprotection. Solvent removal and purification by preparative HPLC, (C 18-reversed phase, acetonitrile—water—trifluoroacetic acid (30:70:0.1) gave the title product (0.0082 g, 54%) as pale yellow solid after freez drying.

¹H-NMR (400 MHz, CD₃OD): δ 1.79 (2H, p, J 7.8 Hz), 1.95 (2H, p, J 7.8 Hz), 3.04 (2H, t, J 7.8 Hz), 3.50 (3H, s), 3.89 (2H, t, J 6.8 Hz), 6.48 (1H, s), 7.00 (1H, t, J 7.9 Hz), 7.05 (1H, t, J 7.0 Hz), 7.13–7.19 (2H, m), 7.24 (1H, d, J 8.0 Hz), 7.26–7.30 (2H, m), 7.42 (1H, d, J 8.2Hz), 7.62(1H, d, J 8.0Hz).

FAB-MS: m/z 400 [MH+].

EXAMPLE 4

5-[1-(3-Aminopropyl)-3-indolyl]-1-(3-indolyl)-1,3-dihydroimidazol-2-one trifluoroacetic acid salt a) 3-[3-(2-{1-[3-(1,3-Dioxo-1,3-dihydroisoindol-2-yl)-propyl]-3-indolyl}-2-oxo-ethyl)ureido]-1-(ethoxycarbonyl)indole The sub-title product, obtained as a white solid, was prepared in 63% yield following the procedure of Example 1 b) starting from the product of Example 1 a) and N-(3-bromopropyl)phthalimide.

¹H-NMR (400 MHz, DMSO-d₆): δ 1.37 (3H, t, J 7.1 Hz), 2.18 (2H, p, J 7.1 Hz), 3.66 (2H, t, J 6.7 Hz), 4.34–4.44 (4H, m), 4.57 (2H, d, J 5.0 Hz), 6.71 (1H, br t, J 5.0 Hz), 7.22–7.40 (4H, m), 7.66 (1H, d, J 8.0 Hz), 7.71 (1H, d, 1 7.7 Hz), 7.80–7.89 (5H, m), 8.09 (1H, br d, J 8.2 Hz), 8.17 (1H, d, J 8.0 Hz), 8.57 (1H, s), 9.12 (1H, s).

FAB-MS: m/z 592 [MH+].

b) 5-(1-[3-{1,3-Dioxo-1,3-dihydroisoindol-2-yl}-propyl]-3-indolyl)-1-[1-(ethoxycarbonyl-3-indolyl]-1,3-dihydroimidazol-2-one The sub-title product, obtained as a off-white solid, was prepared in 99% yield following the procedure of Example 1 c) starting from the product of step a). The product was precipitated from diethyl ether.

¹H-NMR (500 MHz, DMSO-d₆): δ 1.30 (3H, t, J 7.1 Hz), 1.69 (2H, p, J 6.6 Hz), 2.91 (2H, t, J 6.8 Hz), 4.01 (2H, t, J 6.5 Hz), 4.35 (2H, q, J 7.1 Hz), 6.83 (1H, d, J 2.4 Hz), 7.02 (1H, t, J 7.1 Hz), 7.03–7.09 (2H, m), 7.10 (1H, s), 7.13 (2H, t, J 7.5 Hz), 7.40 (1H, d, J 8.2 Hz), 7.66 (1H, d, J 8.0 Hz), 7.80 (1H, s), 7.85 (4H, s), 7.90 (1H, d, J 8.4 Hz), 10.46 (1H, s).

FAB-MS: 574 [MH+], 1147 [MH2+].

The title product, obtained as a off-white solid, was prepared in 66% yield following the procedure of Example 3 f) starting from the product of step b). The product was purified by chromatography on silica, eluting with dichloromethane—methanol—ammonium hydroxide (80:20:2), the free base was treated with diluted trifluoroacetic acid before lyphilisation.

$^1$H-NMR (500 MHz, DMSO-d$_6$): δ 1.76 (2H, p, J 7.3 Hz), 2.47 (2H, p, J 6.7 Hz), 4.00 (2H, t, J 6.8 Hz), 6.71 (1H, s), 6.73 (1H, d, J 2.5 Hz), 6.90 (1H, t, J 7.1 Hz), 7.00 (1H, t, J 7.4 Hz), 7.06 (1H, t, J 7.4 Hz), 7.10–7.14 (2H, m), 7.36–7.39 (2H, m), 7.41 (1H, d, J 8.3 Hz), 7.58 (1H, d, J 8.1 Hz), 7.64 (3H, br s, NH$_3$), 10.29 (1H, s), 11.17 (1H, s).

FAB-MS: m/z 372 [MH+].

EXAMPLE 5

5-[1-(3-Aminopropyl)-3-indolyl]-1-(1-naphthyl)-1,3-dihydroimidazol-2-one trifluoroacetic acid salt.

a) 1-[2-(3-Indolyl)-2-oxoethyl]-3-(1-naphthyl)urea

[2-(3-indolyl)-2-oxoethyl]ammonium bromide (2.00 g, 7.84) was suspended in dry THF (20 ml). Ethyldiisopropylamine (1.40 ml, 7.84 mmol) was added followed by 1-naphthylisocyanate (1.13 ml, 7.84 ml). After stirring for 1 hour the formed precipitated was removed by filtration and washed with THF followed by water to give the sub-title product (2.33 g, 87%) as a white solid after drying.

$^1$H-NMR (400 MHz, DMSO-d$_6$): δ 4.63 (2H, s), 7.11 (1H, br t, J 4.8 Hz), 7.19–7.27 (2H, m), 7.43 (1H, t, J 8.0 Hz), 7.48–7.60 (4H, m), 7.90 (1H, d, J 7.7 Hz), 8.05 (1H, d, J 7.7 Hz), 8.18–8.25 (2H, m), 8.49 (1H, br d, J 2.9 Hz), 8.94 (1H, s), 12.06 (1H, br s).

FAB-MS: m/z 344 [MH+].

b) 1-[2-(1-[3-(1,3-Dioxo-1,3-dihydroisoindol-2-yl)-propyl]-3-indolyl)-2-oxoethyl]-3-(1-naphthyl)urea The sub-title product, obtained as a white solid, was prepared in 85% yield following the procedure of Example 1 b) starting from the product of step a) and N-(3-bromopropyl)phthalimide.

$^1$H-NMR (400 MHz, DMSO-d$_6$): δ 2.19 (2H, p, J 6.9 Hz), 3.67 (2H, t, J 6.7 Hz), 4.37 (2H, t, J 7.3 Hz), 4.61 (2H, d, J 4.8 Hz), 7.11 (1H, br t, J 4.8 Hz), 7.22–7.32 (2H, m), 7.42 (1H, t, J 8.0 Hz), 7.49–7.59 (3H, m), 7.66 (1H, d), 7.80–7.91 (5H, m), 8.04 (1H, d), 8.18–8.22 (2H, m), 8.58 (1H, s), 8.93 (1H, s).

FAB-MS: m/z 531 [MH+].

c) 5-[1-(1,3-Dioxo-1,3-dihydro-isoindol-2-yl)-propyl]-3-indolyl]-1-(1-naphthyl)-1,3-dihydroimidazol-2-one The sub-title product, obtained as an off-white solid, was prepared in 60% yield following the procedure of Example 1 c) starting from the product of step b).

$^1$H-NMR (400 MHz, DMSO-d$_6$): δ 1.68 (2H, p, J 6.7 Hz), 3.10 (2H, dp, J 7.1, 38.8 Hz), 3.91 (2H, t, J 6.7 Hz), 6.47 (1H, s), 6.68 (1H, d, J 2.4 Hz), 6.98 (1H, t, J 7.4 Hz), 7.08 (1H, t, J 7.8 Hz), 7.31–7.45 (3H, m), 7.46–7.62 (4H, m), 7.81–7.91 (6H, m), 10.46 (1H, br s).

FAB-MS: m/z 513 [MH+].

The title compound, obtained as a off-white solid, was prepared in 77% yield following the product of Example 3 f) starting from the product of step c). The product was purified by chromatography on silica, eluting with dichloromethane—methanol—ammonium hydroxide (80:20:2).

$^1$H-NMR (400 MHz, CD$_3$OD): δ 1.77 (2H, p, J 7.4 Hz), 2.29–2.44 (2H, m), 3.88 (2H, t, J 6.7 Hz), 6.26 (1H, s), 6.87 (1H, s), 7.05 (1H, t, J 7.2 Hz), 7.14 (1H, t, J 7.2 Hz), 7.26 (1H, d, J 8.3 Hz), 7.37–7.54 (4H, m), 7.62 (2H, d, J 8.1 Hz), 7.90 (1H, d, J 8.1 Hz), 7.93 (1H, d, J 8.1 Hz).

FAB-MS: m/z 383 [MH+].

EXAMPLE 6

5-[1-(3-Aminopropyl)-3-indolyl]-1-(3-benzo[b]thiophenyl)-1,3-dihydroimidazol-2-one acetic acid salt a) 1-[2-(3-Indolyl)-2-oxoethyl]-3-(3-benzo[b]thiophenyl)urea The sub-title compound was prepared in 85% yield as a white solid following the procedure of Example 1 a) starting from 3-azidocarbonyl-benzo[b]thiophene [Galvez, C. et al. Synthesis (1983) 932–933].

$^1$H-NMR (400 MHz, DMSO-d$_6$): δ 4.63 (2H, d, J 4.9Hz), 6.88 (1H, t, J 4.9Hz), 7.19–7.22 (2H, m), 7.34–7.54 (4H, m), 7.95 (2H, t, J 8.0Hz), 8.17–8.22 (1H, m), 8.49 (1H, d, J 2.9Hz), 9.24 (1H, s), 12.06 (1H, s).

b) 3-[3-(2-{1-[3-(1,3-Dioxo-1,3-dihydroisoindol-2-yl)-propyl]-3-indolyl-}2-oxo-ethyl)ureido]-benzo[b]thiophene The sub-title product, obtained as a white solid, was prepared in quantitative yield following the procedure of Example 1 b) starting from the product of step a) and N-(3-bromopropyl)phthalimide.

$^1$H-NMR (500 MHz, DMSO-d$_6$): δ 2.19 (2H, p, J 7.1 Hz), 3.66 (2H, t, J 6.9 Hz), 4.37 (2H, t, J 7.1 Hz), 4.60 (2H, d, J 5.1 Hz), 6.87 (1H, t, J 5.1 Hz), 7.26 (2H, dt, J 7.6, 20.4 Hz), 7.39 (1H, t, J 7.5 Hz), 7.46 (1H, t, J 7.9 Hz), 7.62 (1H, s), 7.66 (1H, d, J 7.9 Hz), 7.81–7.8 (4H, m), 7.94 (2H, t, J 7.7 Hz), 8.18 (1H, d, J 7.1 Hz), 8.58 (1H, s), 9.23 (1H, s).

FAB-MS: m/z 537.1 [MH+].

c) 5-[1-(1,3-Dioxo-1,3-dihydroisoindol-2-yl)-propyl]-3-indolyl]-1-(3-benzo[b]thiophenyl)-1,3-dihydroimidazol-2-one The sub-title product, obtained as a off-white solid, was prepared in 30% yield following the procedure of Example 1 c) starting from the product of step b).

$^1$H-NMR (500 MHz, CDCl$_3$): δ 1.89 (2H, p, J 6.7 Hz), 3.29 (2H, t, J 6.7 Hz), 3.94 (2H, t, J 6.7 Hz), 6.53 (1H, s), 6.66 (1H, s), 7.12 (1H, t, J 7.5 Hz), 7.15–7.32 (4H, m), 7.55 (1H, s), 7.61 (2H, dd, J 8.1, 12.2 Hz), 7.70–7.78 (3H, m), 7.82–7.90 (2H, m), 10.93 (1H, s).

FAB-MS: m/z 519.1 [MH+].

The title compound, obtained as an off-white solid, was prepared in 50% yield following the procedure of Example 3 f) starting from the product of step c). The product was purified by chromatography on silica, eluting with dichloromethane—methanol—ammonium hydroxide (80:20:2).

$^1$H-NMR (500 MHz, DMSO-d$_6$): δ 1.50 (2H, p, J 6.7 Hz), 1.86 (3H, s), 2.10 (2H, t, J 6.7 Hz), 3.97 (2H, t, J 6.7 Hz), 6.63 (1H, s), 6.83 (1H, s), 6.99 (1H, t, J 7.1 Hz), 7.10 (1H, t, J 7.1 Hz), 7.28 (1H, t, J 7.6 Hz), 7.32–7.40 (3H, m), 7.57 (1H, d, J 7.9 Hz), 7.82 (1H, s), 7.98 (1H, s,J 7.9 Hz), 10.44(br s, 1H).

FAB-MS: m/z 389.1 [MH+].

EXAMPLE 7

5-[1-{3-(Aminomethyl)benzyl}-3-indolyl]-1-(3-indolyl)-1,3-dihydroimidazol-2-one trifluoroacetic acid salt The title product, obtained as an off-white solid, was prepared following the procedure of Example 4 starting from N-[3-(bromomethyl)benzyl]phthalimide.

$^1$H-NMR (400 MHz, CD$_3$OD): δ 3.90 (2H, s), 5.05 (2H, s), 6.51 (1H, d, J 7.3 Hz), 6.60 (1H, s), 6.77 (1H, s), 6.84–6.97 (2H, m), 6.99–7.18 (5H, m), 7.18–7.26 (2H, m), 7.31 (1H, s), 7.34 (1H, d, J 8.5 Hz), 7.64 (1H, br d, J 8.0 Hz).

FAB-MS: m/z 434 [MH+].

EXAMPLE 8

5-[1-(3-Aminopropyl)-3-indolyl]-1-(3-indolyl)-5-methyl-1,3-dihydroimidazol-2-one a) 3-{3-[(2S)-1-(3-Indolyl)-1-oxo-2-proyl]ureido}-1-(ethoxycarbonyl)indole The sub-title compound was prepared in 50% yield as a white solid following the procedure of Example 1 a) starting from 2S-[1-(3-indolyl)-1-oxopropyl]-2-ammonium chloride.

¹H-NMR (400 MHz, DMSO-d₆): δ 1.37 (3H, t, J 6.7 Hz), 1.41 (3H, d, J 7.0 Hz), 4.40 (2H, q, J 7.0 Hz), 5.21 (1H, p, J 7.3 Hz), 6.86 (1H, d, J 7.6 Hz), 7.19–7.27 (2H, m), 7.32 (1H, t, J 7.4 Hz), 7.38 (1H, t, J 7.5 Hz), 7.50 (1H, d, J 6.8 Hz), 7.67 (1H, d, J 7.7 Hz), 7.81 (1H, s), 8.10 (1H, br d, J 7.8 Hz), 8.21 (1H, d, J 7.3 Hz), 8.53 (1H, d, J 3.2 Hz), 8.99 (1H, s), 12.11 (1H, br s, indole NH).

FAB-MS: m/z 419 [MH+].

The title compound, obtained as a yellow solid, was prepared following the procedure of Example 4 starting from the product of step a). The product was purified by chromatography on silica, eluting with dichloromethane—methanol—ammonium hydroxide (80:20:2), followed by purification by preparative HPLC, C18-reversed phase, acetonitrile—water—trifluoroacetic acid (30:70:0.1).

¹H-NMR (500 MHz, CD₃OD): δ 1.89 (2H, dt, J 6.8, 15.7 Hz), 2.12 (3H, s), 2.38 (2H, br t, J 8.2 Hz), 4.08 (2H, t, J 6.6 Hz), 6.86 (1H, t, J 7.6 Hz), 6.88 (1H, s), 7.01 (1H, t, J 7.3 Hz), 7.03 (1H, t, J 7.7 Hz), 7.13 (1H, t, J 7.9 Hz), 7.17 (1H, s), 7.19 (1H, d, J 7.9 Hz), 7.28 (1H, d, J 8.2 Hz), 7.31 (1H, d, J 8.2 Hz), 7.39 (1H, d, J 8.0 Hz).

EXAMPLE 9

5-[1-(3-Hydroxypropyl)-3-indolyl]-1-(3-indolyl)-1,3-dihydroimidazol-2-one

The title compound, obtained as an off-white solid, was prepared following the procedure of Example 4 starting from O-acetyl-3-brompropanol.

¹H-NMR (400 MHz, CDCl₃): δ 1.61 (2H, p, J 6.2 Hz), 2.77 (2H, t, J 5.7 Hz), 3.95 (2H, t, J 6.4 Hz), 6.41 (1H, s), 6.68 (1H, d, J 2.2 Hz), 7.00 (1H, t, J 7.3 Hz), 7.12–7.37 (7H, m), 7.73 (1H, d, J 7.7Hz), 8.57 (1H, br s), 8.74 (1H, br s).

FAB-MS: m/z 473.1 [MH+].

EXAMPLE 9b 5-(8-Hydroxymethyl-6,7,8,9-tetrahydropyrido[1,2-a]indol-10-yl)-1-(3-indolyl)-1,3-dihydroimidazol-2-one The title compound, obtained as a off-white solid, was prepared following the procedure of Example 2 starting from 2-(8-acetoxymethyl-6,7,8,9-tetrahydropyrido[1,2-a]indol-10-yl)-2-oxoethylammonium chloride. Prepared according to the procedure described by Bergman et al. Tetrahedron 29 (1973) 971–976, starting from acetic acid 6,7,8,9,-tetrahydropyridol[1,2-a]indol-8-ylmethyl ester.

¹H-NMR (500 MHz, CDO₃D): δ 1.55–1.66 (1H, m), 1.70–1.79 (1H, m), 2.05–2.21 (2H, m), 2.91 (1H, dd, J 3.9, 16.4 Hz), 3.33–3.40 (2H, m), 3.72 (1H, dt, J 5.0, 11.6 Hz), 4.13–4.19 (1H, m), 5.50 (1H, s), 6.56 (1H, s), 6.89–6.96 (2H, m), 6.97–7.07 (3H, m), 7.18 (1H, d, J 8.1 Hz), 7.23–7.35 (3H, m).

FAB-MS: m/z 399 [MH+].

EXAMPLE 10

1-[1-{3-(Aminomethyl)benzyl}-3-indolyl]-5-(1-methyl-3-indolyl)-1,3-dihydroimidazol-2-one acetic acid salt The title compound was prepared following the procedure outlined in Example 3 starting from the product of Example 3 e) and N-[3-(bromomethyl)benzyl]phthalimide.

FAB-MS: m/z 448 [MH+].

EXAMPLE 11

5-[1-(3-Amidinothiopropyl)-3-indolyl]-1-(3-indolyl)-1,3-dihydroimidazol-2-one acetic acid salt The product from Example 9 (0.062 g, 0.16 mmol), pyridine (0.4 mol) and methanesulphonic anhydride (0.037 g, 0.21 mmol) was dissolved in dichloromethane (30 ml) and stirred for 4 hours at room temperature. The reaction was quenched by treatment of the organic phase with sulfuric acid (1M, 40 ml). The phases were separated and the organic phase washed with brine (1×40 ml) and dried over Na₂SO₄. After removal of the solvent in vacuu the crude methanesulphonate was used directly. The crude methanesulphonate was treated with thiourea (0.025 g, 0.33 mmol) in refluxing absolute ethanol (40 ml) for 18 hours. The solvent was removed and the residue purified by chromatograph on silica, eluting with dichlormethane—methanol—triethylamine (first 90:10:1 then 80:20:1), to give the 5-[1-(3-Amidinothiopropyl)-3-indolyl]-1-(3-indolyl)-1,3-dihydroimidazol-2-one (0.018 g, 25%).

The product was converted to the title compound by dissolving it in acetic acid (1 M) followed by lyophilization.

¹H-NMR (400 MHz, DMSO-d₆): δ 1.69 (2H, p, J 7.1 Hz), 2.46 (2H, t, J 7.3 Hz), 3.97 (2H, t, J 7.0 Hz), 6.64 (1H, s), 6.75 (1H, s), 6.86 (1H, t, J 7.4 Hz), 6.97–7.15 (4H, m), 7.37 (2H, dd, J 8.2 Hz), 7.41 (1H, s), 7.59 (1H, d, J 8.1 Hz), 10.26 (1H, s), 11.21 (1H, s).

FAB-MS: m/z 431 [MH+].

EXAMPLE 11b 5-(8-Amidinothiomethyl-6,7,8,9-tetrahydropyrido[1,2-a]indol-10-yl)-1-(3-indolyl)-1,3-dihydroimidazol-2-one acetic acid salt The title compound was prepared following the procedure of Example 11 starting from the product of Example 9 b).

¹H-NMR (500 MHz, CDO₃D): δ 1.66–1.78 (1H, m), 1.84–1.94 (1H, m), 2.15–2.28 (2H, m), 2.91 (1H, dd, J 7.6, 13.4Hz), 3.00–3.07 (1H, m), 3.12 (1H, dd, J 7.0, 13.2Hz), 3.76 (1H, dt, J 5.1, 11.5Hz), 4.16–4.23 (1H, m), 6.59 (1H, s), 6.93 (1H, t, J 7.8Hz), 6.98 (1H, t, J 7.8 Hz), 7.03–7.08 (3H, m), 7.21 (1H, d, J 8.0Hz), 7.28 (2H, d, J 8.4Hz), 7.38 (1H, d, J 8.0 Hz).

FAB-MS: m/z 457 [MH+].

EXAMPLE 12

1-(1-Ethoxycarbonyl-3-indolyl)-5-(3-indolyl)-4-methyl-1,3-dihydroimidazol-2-one

The title compound was prepared in 88% yield following the procedure of Example 2 a) starting from the product of Example 8 a).

¹H-NMR (400 MHz, DMSO-d₆): δ 1.33 (3H, t, J 7.1 Hz), 1.98 (3H, s), 4.39 (2H, q, J 7.1 Hz), 6.90 (1H, t, J 7.3 Hz), 7.01 (1H, t, J 7.9 Hz), 7.09 (1H, t, J 7.4 Hz), 7.18 (1H, d, J 2.6 Hz), 7.23–7.32 (4H, m), 7.58 (1H, s), 7.98 (1H, d, J 8.7 Hz), 10.38 (1H, s, NH), 11.10 br s, indole NH).

FAB-MS: m/z 401 [MH+].

EXAMPLE 13

1,5-Bis-(3-indolyl)-4-methyl-1,3-dihydroimidazol-2-one

The title product was prepared following the procedure of Example 2 starting from the product of Example 12. The product was precipitated from diethyl ether.

¹H-NMR (400 MHz, DMSO-d₆): δ 1.97 (3H, s), 6.87 (2H, t, J 7.6 Hz), 6.96–7.03 (2H, m), 7.17–7.21 (2H, m), 7.25 (2H, t, J 6.8 Hz), 7.28 (1H, d, J 8.4 Hz), 10.16 (1H, s, NH), 10.95 (1H, s, indole NH), 11.02 (1H, s, indole NH).

FAB-MS: m/z 329 [MH+].

EXAMPLE 14

5-(3-Indolyl)-1-(1-naphthyl)-1,3-dihydroimidazol-2-one

The title compound, obtained as an off-white solid, was prepared in 57% yield following the procedure of Example 2 a) starting from the product of Example 5 a).

$^1$H-NMR (400 MHz, DMSO-$d_6$): δ 6.21 (1H, d, J 2.8 Hz), 6.92 (1H, d, J 2.4 Hz), 6.98 (1H, t, J 6.9 Hz), 7.05 (1H, t, J 6.9 Hz), 7.23 (1H, d, J 8.0 Hz), 7.46–7.59 (5H, m), 7.65 (1H, d, J 7.9 Hz), 8.00 (2H, d, J 7.5 Hz), 10.45 (1H, br s), 10.79 (1H, br s).

FAB-MS: m/z 325 [MH+].

EXAMPLE 15

1-(3-Benzo[b]thiophenyl)-5-(3-indolyl)-1,3-dihydroimidazol-2-one

The title compound, obtained as a off-white solid, was prepared in 80% yield following the procedure of Example 2 a) starting from the product of Example 6 a).

$^1$H-NMR (400 MHz, CDCl$_3$): δ 6.41 (1H, s), 6.72 (1H, s), 7.11–7.23 (2H, m), 7.27–7.39 (3H, m), 7.43 (1H, s), 7.62 (2H, t, J 7.7 Hz), 7.82 (1H, d, J 7.8 Hz), 8.04 (1H, s), 10.42 (1H, s).

FAB-MS: m/z 332.0 [MH+].

EXAMPLE 16

1-(1-Ethoxycarbonyl-3-indolyl)-5-(5-methoxy-3-indolyl)-1,3-dihydroimiidazol-2-one The title compound was prepared following the procedure of Example 2 a) starting from [2-(5-methoxy-3-indolyl)-2-oxoethyl]ammonium chloride.

$^1$H-NMR (500 MHz, DMSO-$d_6$): δ 1.35 (3H, t, J 7.2 Hz), 3.55 (3H, s), 4.41 (2H, q, J 7.3 Hz), 6.65 (1H, d, J 9.2 Hz), 6.75 (1H, s), 6.85 (1H, s), 6.92 (1H, s), 7.15–7.18 (2H, m), 7.27 (1H, d, J 7.8 Hz), 7.33 (1H, t, J 7.1 Hz), 7.73 (1H, s), 8.08 (1H, d, J 9.0 Hz), 10.40 (1H, s), 10.84 (1H, s).

FAB-MS: m/z 417 [MH+].

EXAMPLE 17

5-[1-{3-(Aminomethyl)benzyl}-3-indolyl]-1-(3-benzo[b]thiophenyl)-4-(ethoxycarbonyl)-2,3-dihydroimidazole-2-one acetic acid salt The title product was prepared as described in Example 9 starting from 2-amino-3-(3-indolyl)-3-oxo-propionic acid methyl ester hydrochloride and 3-azidocarbonyl-benzo[b]thiophene.

$^1$H-NMR (400 MHz, CD$_3$OD): δ 3.68 (3H, s), 3.88 (2H, s), 5.21 (2H, s), 6.48 (1H, d J 7.2), 6.93 (1H, t J 8.0), 6.98–7.06 (2H, m), 7.09–7.25 (6H, m), 7.26–7.34 (2H, m), 7.45 (1H, d J 7.8), 7.57 (1H, s), 7.78 (1H, d J 8.8).

FAB-MS: m/z: 509.1 [MH+].

EXAMPLE 18

4-(Ethoxycarbonyl)-5-(1-methyl-3-indolyl)-1-(1-naphthyl)-2,3-dihydroimidazole-2-one The title compound was prepared as described in Example 14 starting from 2-amino-3-(3-indolyl)-3-oxo-propionic acid ethyl ester hydrochloride.

$^1$H-NMR (500 MHz, CDCl$_3$): δ 0.98 (3H, t J 7.1 Hz), 3.49 (3H, s), 4.11–4.20 (2H, m), 6.60 (1H, s), 7.02–7.07 (1H, m), 7.15 (2H, d, J 4.2), 7.30–7.39 (3H, m), 7.46–7.53 (2H, m), 7.74–7.87 (3H, m), 8.87 (1H, br s).

FAB-MS: m/z: 412.2 [MH+], 823.2 [MH2+], 845.1 [MNa2+].

EXAMPLE 19

1,5-Bis-(3-indolyl)-5-(trifluoromethyl)-1,3-dihydroimidazol-2-one

The title product was prepared following the procedure of Example 2 starting 2-amino-3,3,3-trifluoro-1-(3-indolyl)-propan-1-one.

$^1$H-NMR (500 MHz, DMSO-$d_6$): δ 6.87–6.93 (2H, m), 7.01 (2H, q, J 7.2 Hz), 7.21–7.27 (3H, m), 7.30–7.36 (3H, m), 11.09 (1H, s), 11.25 (1H, s), 11.45 (1H, s).

FAB-MS: m/z 383 [MH+].

EXAMPLE 20

1,5-Bis-(3-indolyl)-4-phenyl-1,3-dihydroimidazol-2-one

The title product was prepared following the procedure of Example 2 starting 2-amino-1-(3-indolyl)-2-phenylethanone hydrochloride.

$^1$H-NMR (400 MHz, DMSO-$d_6$): δ 6.82 (1H, t, J 7.3 Hz), 6.90 (1H, t, J 7.3 Hz), 6.96–7.05 (2H, m), 7.05–7.18 (4H, m), 7.20 (1H, s), 7.22–7.31 (6H, m), 10.87 (1H, s), 11.01 (1H, br s), 11.11 (1H, br s).

FAB-MS: m/z 391 [MH+].

EXAMPLE 21

5-[1-(3-Aminopropyl)-3-indolyl]-1-(3-indolyl)-4-phenyl-1,3-dihydroimidazol-2-one trifluoroacetic acid salt The title product was prepared following the procedure of Example 4 starting 2-amino-1-(3-indolyl)-2-phenylethanone hydrochloride.

$^1$H-NMR (400 MHz, CD$_3$OD): δ 1.87 (2H, dt, J 6.7, 15.4 Hz), 2.33 (2H, t, J 8.3 Hz), 4.10 (2H, t, J 8.3 Hz), 6.87–6.95 (2H, m), 6.97 (1H, s), 7.06 (1H, t, J 7.6 Hz), 7.11 (1H, t, J 7.6 Hz), 7.14–7.25 (6H, m), 7.28–7.37 (4H, m).

FAB-MS: m/z 448 [MH+].

EXAMPLE 22

5-{1-[3-(N,N-Dimethylamino)propyl]-3-indolyl}-1-(3-indolyl)-1,3-dihydroimidazol-2-one acetic acid salt The title compound was prepared following the procedure of Example 2 starting from 3-(N,N-dimethylamino)propyl chloride hydrocloride and the product of Example 1 a).

$^1$H-NMR (500 MHZ, CD$_3$OD): δ 1.81 (2H, p, J 7.6 Hz), 1.94 (3H, s), 2.45 (6H, s), 3.98 (2H, t, J 6.6 Hz), 6.58 (1H, s), 6.78 (1H, s), 6.95 (1H, t, J 7.6 Hz), 7.08–7.13 (2H, m), 7.16–7.22 (2H, m), 7.34 (1H, d, J 8.1 Hz), 7.35 (1H, s), 7.40 (1H, d, J 8.7 Hz), 7.67 (1H, d, J 8.3 Hz).

FAB-MS: m/z 400 [MH+].

EXAMPLE 23

5-[1-(3-Aminopropyl)3-indolyl]-1-(4-phenoxyphenyl)-1,3-dihydroimidazol-2-one acetic acid salt.

The title compound was prepared following the procedure of Example 5 starting from 4-phenoxyphenylisocyanate.

¹H-NMR (500 MHz, CDCl₃): δ 1.93 (3H, s), 2.09 (2H, p, J 7.8 Hz), 2.79 (2H, t, J 8.1 Hz), 4.21 (2H, t, J 6.7 Hz), 6.65 (1H, s), 6.89 (4H, d, J 8.7 Hz), 6.92 (1H, s), 7.02 (1H, t, J 6.7 Hz), 7.09 (1H, t, J 6.7 Hz), 7.17–7.22 (3H, m), 7.31 (2H, t, J 8.0 Hz), 7.37 (1H, d, J 8.0 Hz), 7.41 (1H, d, J 8.0 Hz).

FAB-MS: m/z 425 [MH+].

EXAMPLE 24

1-[1-(4-Aminobutyl)-3-indolyl]-4-(ethoxycarbonyl)-5-(1-methyl-3-indolyl)-1,3-dihydroimidazol-2-one acetic acid salt The title compound was prepared following the procedure outlined in Example 3 starting from 2-amino-3-(1-methyl-3-indolyl)-3-oxopropionic acid ethyl ester hydrochloride (von Geldern et al. *J. Med. Chem.* 39 (1996) 957–967).

¹H-NMR (400 MHz, CDCl₃): 0.70 (3H, t, J 7.1 Hz), 1.57 (2H, p, J 7.6 Hz), 1.84 (2H, p, J 7.6 Hz), 2.71 (2H, t, J 7.4 Hz), 3.50 (3H, s), 4.00 (2H, q, J 6.9 Hz), 4.23 (2H, t, J 7.1 Hz), 6.72 (1H, s), 6.73 (1H, s), 6.96 (1H, t, J 7.8 Hz), 7.01–7.09 (2H, m), 7.11–7.19 (3H, m), 7.26 (1H, d, J 8. 1 Hz), 7.37 (1H, d, J 7.8 Hz), 9.46 (1H, bs). (obtained for the free amine)

FAB-MS m/z: 472.2 [MH+].

EXAMPLE 25

5-[1-(3-Aminopropyl)-3-indolyl]-4-carbamoyl-1-(benzo[b]thiophen-3-yl)-2,3-dihydroimidazole-2-one acetic acid salt The title compound was prepared following the procedure outlined in Example 4 starting from 2-amino-3-(1-methyl-3-indolyl)-3-oxopropionic amide hydrochloride prepared in analogy with von Geldern et al. *J. Med. Chem.* 39 (1996) 957–967.

¹H-NMR (400 MHz, DMSO-d₆): δ 0.95–1.08 (2H, m), 1.48–1.58 (2H, m), 2.43–2.47 (2H, m), 4.03 (2H, t, J 6.3 Hz), 6.95 (1H, t, J 8.2 Hz), 7.10 (1H, t, J 8.2 Hz), 7.21–7.33 (3H, m), 7.35–7.45 (3H, m), 7.86–7.94 (2H, m).

FAB-MS m/z: 428.0 [MH+].

EXAMPLE 26

5-[3-(Aminopropyl)-3-indolyl]-4-benzyl-1-(3-indolyl)-1,3-dihydroimidazol-2-one acetic acid salt a) 2-(N-tert-Butoxycarbonylamino)-1-{1-[3-(1,3-dioxo-1,3-dihydroisoindol-2-yl)-propyl]-3-indolyl}-3-phenyl-1-propanone 2-(N-tert-butoxycarbonylamino)-1-{1-[3-(1,3-dioxo-1,3-dihydroisoindol-2-yl)-propyl]-3-indolyl}-1-ethanone (0.30 g, 0.65 mmol) was dissolved in dry THF (7.5 ml) and cooled to –10° C., sodium bis(trimethylsilyl)amide (0.65 ml, 1 M in THF, 0.65 mmol) was added and the resulting yellow solution stirred for 15 minutes. Benzylbromide (0.16 ml, 1.30 mmol) was added and the stirring continued for 15 minutes at –10° C., the cooling bath was removed and stirring continued for 4 hours. Saturated NH₄Cl(aq) was added followed by removal of the aqueous phase. The organic solvent was evaporated in vacuum and the residue chromatographed furnishing the sub-title product (0.28 g, 79%).

¹H-NMR (400 MHz, CDCl₃): δ 1.42 (9H, s), 2.21 (2H, p, J 6.9 Hz), 3.13–3.25 (1H, dd, J 6.0, 13.6), 3.21 (1H, dd, J 7.3, 13.5), 3.73 (2H, t, J 6.4 Hz), 4.07–4.20 (2H, m), 5.17–5.24 (1H, m), 5.58 (1H, br d, J 7.8 Hz, NH), 7.10–7.23 (5H, m), 7.29–7.35 (3H, m), 7.73 (1H, s), 7.75–7.80 (2H, m), 7.85–7.92 (2H, m), 8.34–8.40 (1H, m). APCI-MS: M/z 452.2 [MH-CO₂ᵗBu].

b) (2-{1-[3-(1,3-dioxo-1,3-dihydroisoindol-2-yl)-propyl]-3-indolyl}-2-oxo-3-phenylpropyl)ammonium chloride The product of step a) (0.15 g, 0.27 mmol) was dissolved in HCl(EtOAc) (3 ml, 3 M) and stirred for 15 minutes. The solvent was removed furnishing the sub-title product (0.13 g, quant) as a white solid.

¹H-NMR (400 MHz, CD₃OD): δ 2.23 (2H, p, J 6.6 Hz), 3.22 (1H, dd, J 7.31, 13.8 Hz), 3.39 (1H, dd, J 7.11, 13.8 Hz), 3.68 (2H, t, J 6.7 Hz), 4.25 (2H, t, J 6.9 Hz), 4.96 (1H, t, J 7.3 Hz), 7.19–7.35 (7H, m), 7.52 (1H, d, J 8.1 Hz), 7.80–7.89 (4H, m), 8.07 (1H, s), 8.25 (1H, d, J 7.72 Hz).

c) 3-[3-(2-{1-[3-(1,3-dioxo-1,3-dihydroisoindol-2-yl)-propyl]-3-indolyl}-2-oxo-3-phenylpropyl)ureido]-1-(ethoxycarbonyl)indole The sub-title product was prepared in 58% yield as a yellow solid following the procedure of Example 1 a) starting from the product of step b). APCI-MS: m/z 682.1 [MH+].

d) 4-benzyl-5-{1-[3-(1,3-dioxo-1,3-dihydroisoindol-2-yl)-propyl]-3-indolyl}-1-[1-(ethoxycarbonyl)-3-indolyl]-1,3-dihydroimidazol-2-one The product of step c) (0.11 g, 0.16 mmol) and scandium (III) trifluoromethane sulfonate (0.06 g, 0.012 mmol) was dissolved in methanol (6 ml). The reaction mixture was heated to 110° C. in a sealed tube for 3.5 hours. The methanol was removed and the residue dissolved in ethyl acetate and filtered through SiO2, the sub title product (0.080 g, 78%) was obtained after removal of solvent.

¹H-NMR (400 MHz, DMSO-d₆): δ 1.25 (3H, t, J 7.1 Hz), 1.85 (2H, p, J 6.7 Hz), 3.14 (2H, t, J 7.0 Hz), 3.71 (2H, s), 4.15 (2H, t, J 6.5 Hz), 4.27 (2H, q, J 7.2 Hz), 6.92 (1H, t, J 7.5 Hz), 7.03–7.09 (2H, m), 7.12–7.24 (4H, m), 7.26–7.37 (4H, m), 7.40 (1 H, d, J 8.2 Hz), 7.45 (1H, s), 7.62 (1H, s), 7.82–7.89 (5H, m). APCI-MS: m/z 664.1 [MH+].

e) The title product, obtained as an off-white solid, was prepared in 57% yield following the procedure of Example 4 b) starting from the product of step d).

¹H-NMR (400 MHz, DMSO-d₆): δ 1.64 (2H, p, J 6.6 Hz), 1.86 (3H, s), 2.21 (2H, t, J 6.7 Hz), 3.66 (2H, s), 4.10 (2H, t, J 6.7 Hz), 6.82–6.91 (2H, m), 6.96–7.05 (2H, m), 7.16–7.32 (10H, m), 7.35 (1H, d, J 8.3Hz), 10.29 (1H, br s, NH), 11.01 (1H, br s, NH).

FAB-MS: m/z 462.2 [MH+].

EXAMPLE 27

5-[3-(Aminopropyl)-3-indolyl]-1-(3-indolyl)-4-[(N-methylcarboxamid)methyl]-1,3-dihydroimidazol-2-one trifluoroacetic acid salt The title product, obtained as an off-white solid, was prepared following the procedure of Example 26, with the exception that acetic acid was used instead of scandiumtriflate/methanol, starting from 2-(N-tert-butoxycarbonylamino)-1-{1-[3-(1,3-dioxo-1,3-dihydroisoindol-2-yl)-propyl]-3-indolyl}-1-ethanone and ethyl bromacetate.

FAB-MS: m/z 443.3 [MH+].

What is claimed is:

1. A compound of formula (I):

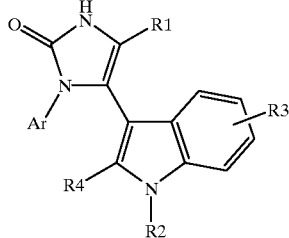

(I)

wherein:
Ar is an optionally substituted, aromatic or heteroaromatic group,
R1 is H, $C_{1-6}$alkyl, fluoro substituted $C_{1-6}$ alkyl, phenyl, benzyl, carbo$C_{1-6}$alkoxy, carbamoyl, or methyl(N—$C_{1-6}$alkylcarbamoyl),
R2 is H, $C_{1-6}$alkyl, amino$C_{1-6}$alkyl, hydroxy$C_{1-6}$alkyl, (mono- or di-$C_{1-6}$alkyl)amino$C_{1-6}$alkyl, (amino$C_{1-3}$alkylphenyl)$C_{1-3}$alkyl, or amidinothio$C_{1-6}$alkyl,
R3 is H or $C_{1-6}$alkoxy,
R4 is H or together with R2, forms an annulated ring which may be substituted by hydroxy$C_{1-3}$alkyl amidinothio$C_{1-3}$alkyl, or amino$C_{1-3}$alkyl;
or a salt thereof.

2. A compound according to claim 1, wherein
Ar is an optionally substituted bicyclic aromatic or an optionally substituted bicyclic heteroaromatic group,
R1 is H, methyl, or $CF_3$, and
R3 is H or methoxy,
provided that when R4 is H, R2 is H, methyl, aminopropyl, hydroxypropyl or amidinothiopropyl, and further provided that wheh R2 and R4 together form an annulated ring, they together comprise 4 or 5 carbons.

3. A compound according to claim 1; wherein Ar comprises a single heteroatom.

4. A compound according to claim 3; wherein the heteroatom is N, O or S.

5. A compound according to claim 1, wherein Ar is selected from benzothiophene, naphthyl, phenoxyphenyl, or indolyl optionally substituted with aininobutyl, aminomethyl benzyl, ethoxy carbonyl, or 2,2,2 trichoroethyl carbonyl.

6. A compound selected from the group consisting of:
1-(3-Indolyl)-5-(1-methyl-3-indolyl)-1,3-dihydroimidazol-2-one,
1,5-Bis-(3-indolyl)-1,3-dihydroimidazol-2-one,
1-[1-(4-Aminobuty1)-3-indolyl]-5-(1-methyl-3-indolyl)-1,3-dihydroimidazol-2-one,
5-[1-(3-Aminopropyl)-3-indolyl]-1-(3-indolyl)-1,3-dihydroimidazol-2-one,
5-[1-(3-Aminopropyl)-3-indolyl]-1-(3-benzo[b]thiophenyl-1,3-dihydroimidazol-2-one,
5-[1-(3-Aminopropyl)-3-indolyl]-1-(1-naphthyl)-1,3-dihydroimidazol-2-one,
5-[1-{3-(Aminomethyl)benzyl}-3-indolyl]-1-(3-indolyl)-1,3-dihydroimidazol-2-one,
5-[1-(3-Aminopropyl)-3-indolyl]-1-(3-indolyl)-4-methyl-1,3-dihydroimidazol-2-one,
5-(3-Indolyl)-1-(1-naphthyl)-1,3-dihydroimidazol-2-one,
1-(3-Benzo[b]thiophenyl)-5-(3-indolyl)-1,3-dihydroimidazol-2-one,
5-[1-{3-(Aminomethyl)benzyl}-3-indolyl]-1-(3-benzo[b]tbiophenyl)-4-(ethoxycarbonyl)-2,3-dihydroimidazole-2-one,
4-(Ethoxycarbonyl)-5-(1-methyl-3-indolyl)-1-(1-naphthyl)-2,3-dihydroimidazole-2-one,
1,5-Bis-(3-indolyl)-5-(trifluoromethyl)-1,3-dihydroimidazol-2-one,
1,5-Bis-(3-indolyl)-4-phenyl-1,3-dihydroimidazol-2-one,
5-[1-(3-Aminopropyl)-3-indolyl]-1-(3-indolyl)-4-phenyl-1,3-dihydroimidazol-2-one;
1-(1-Ethoxycarbonyl-3-indolyl)-5-(5-methoxy-3-indolyl)-1,3-dihydroimidazol-2-one,
5-{1-[3-(N,N-Dimethylamino)propyl]-3-indolyl}-1-(3-indolyl)-1,3-dihydroimidazol-2-one,
5-[1-(3-Aminopropyl)-3-indolyl]-1-(4-phenoxyphenyl)-1,3-dibydroimidazol-2-one,
5-(8-Amidinothiomethyl-6,7,8,9-tetrahydropyrido[1,2-a]lindol-10-yl)-1-(3-indolyl)-1,3-dihydroimidazol-2-one,
5-(8-Hydroxymethyl-6,7,8,9-tetrahydropyrido[1,2-a]lindol-10-yl)-1-(3-indolyl)-1,3-dihydroimidazol-2-one,
1-[1-(4-Aminobutyl)-3-indolyl]-4-(ethoxycarbonyl)-5-(1-metlhyl-3-indolyl)-1,3-dihydroimidazol-2-one,
5-[1-(3-Aminopropyl)-3-indolyl]-4-carbamoyl-1-(benzo[b]thiophen-3-yl)-2,3-dihydroimidazole-2-one,
5-[3-(Aminopropyl)-3-indolyl]-4-benzyl-1-(3-indolyl)-1,3-dihydroimidazol-2-one, and
5-[3-(Aminopropyl)-3-indolyl]-1-(3-indolyl)-4-[(N-methylcarboxamido)methyl]-1,3-dihydroimidazol-2-one,
or a salt thereof.

7. A pharmaceutically acceptable salt of a compound as claimed in claim 1.

8. A pharmaceutical formulation comprising a compound as claimed in claim 1 or a salt as claimed in claim 7; and a pharmaceutically acceptable carrier therefor.

9. A process for the synthesis of a compound of formula (I) comprising:

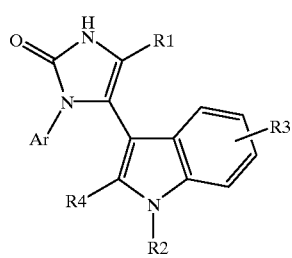

(I)

wherein Ar, R1, R2, R3 and R4 are as defined in claim 1, comprising
converting a compound of formula (I), to a pharmaceutically acceptable salt thereof, or vice versa; or converting a pharmaceutically acceptable salt of a compound of formula (I) into a different pharmaceutically acceptable salt; or intramolecular condensation of a compound of formula (III):

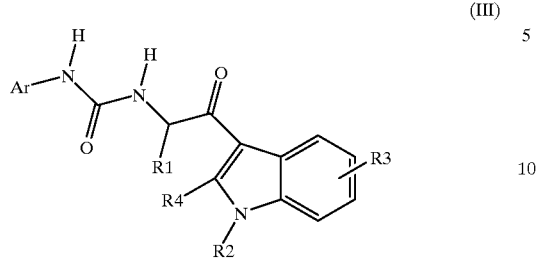

(III)

wherein Ar, R1, R2, R3 and R4 are as defined for formula (I); or for compounds of formula (I) wherein Ar carries a functional group which might be sensitive for or interfere with the reaction conditions during the intramolecular condensation (III), by intramolecular condensation of a corresponding compound of formula (III), but in which the functional groups on Ar are suitably protected, followed by subsequent deprotection; or for compounds of formula (I), wherein at least one of $R_2$ or Ar carries an amino, or hydroxy group, by deprotection of a compound of formula (II) corresponding to formula (I) but in which at least one of $R_2$ or Ar carries a protected amino or hydroxy group, or for compounds of formula (I) wherein R2 is alkyl and Ar is an indole, substituted on the indole nitrogen with an alkyl carrying an amino or hydroxy group, may be prepared by deprotecting a compound of formula (V) in which R5 is an alkyl carrying a protected amino or hydroxy group

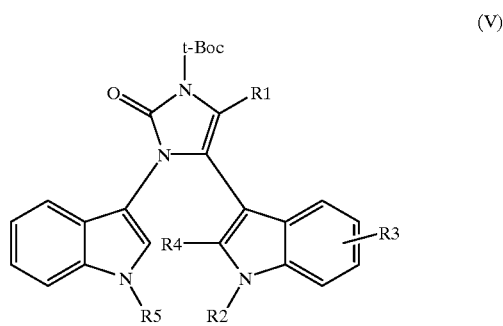

(V)

wherein R1, R2, R3, and R4 are as defined for formula (I).

10. A pharmaceutical formulation comprising a compound as claimed in claim 6 and a pharmaceutically acceptable carrier.

11. A method of treating inflammatory disorders comprising administrating to an individual requiring such therapy a therapeutically effective amount of a compound as claimed in claim 1.

12. A method of treating inflamnmatory disorders comprising administrating to an individual requiring such therapy a therapeutically effective amount of a compound as claimed in claim 6.

* * * * *

UNITED STATES PATENT AND TRADEMARK OFFICE
CERTIFICATE OF CORRECTION

| | | |
|---|---|---|
| PATENT NO. | : 6,337,342 B1 | Page 1 of 2 |
| DATED | : January 8, 2002 | |
| INVENTOR(S) | : Kostas Karabelas, Matti Lepistö and Peter Sjö | |

It is certified that error appears in the above-identified patent and that said Letters Patent is hereby corrected as shown below:

Title page,
Item [75], Inventors, delete "Matti Lepisto" and insert -- Matti Lepistö --.
Item [30], Foreign Application Priority Data, delete "9704874" and insert -- 9704874-8 --; and delete "9802539" and insert -- 9802539-8 --.
Item [56], U.S. PATENT DOCUMENTS, delete "Welsted, Jr." and insert -- Welstead, Jr. --; and
delete "Huebner" and insert -- Huebner, et al. --.
OTHER PUBLICATIONS, "Galzunov" reference, delete "Bicochemical Study" and insert -- Biochemical Study --.

Column 5,
Line 65, delete "10 gm" and insert -- 10$\mu$m --.

Column 7,
Line 23, delete "8.0Hz" and insert -- 8.0 Hz --.
Line 55, delete "generally' about" and insert -- generally about --.

Column 12,
Line 16, delete "7.81-7.8" and insert -- 7.81-7.89 --.

Column 14,
Line 52, delete "11.10 br s," and insert -- 11.10 (1H, br s, --.

Column 15,
Line 32, delete "dihydroimiidazol" and insert -- dihydroimidazol --.

Column 17,
Line 66, delete "7.8 Hz, NH)" and insert -- 7.8 Hz, N<u>H</u>) --.

UNITED STATES PATENT AND TRADEMARK OFFICE
CERTIFICATE OF CORRECTION

PATENT NO. : 6,337,342 B1
DATED : January 8, 2002
INVENTOR(S) : Kostas Karabelas, Matti Lepistö and Peter Sjö

It is certified that error appears in the above-identified patent and that said Letters Patent is hereby corrected as shown below:

Column 19,
Line 39, delete "that wheh" and insert -- that when --.
Line 48, delete "aininobutyl," and insert -- aminobutyl --.
Line 49, delete "trichoroethyl" and insert -- trichloroethyl --.
Line 55, delete "Aminobutyl)" and insert -- Aminobutyl) --.
Line 67, after "5-[1-(3-Aminopropyl)-3-indolyl]-1-(3-indolyl)-4-methyl-1,3-dihydroimidazol-2-one," please insert the following: -- 5-[1-(3-Hydroxypropyl)-3-indolyl]-1-(3-indolyl)-1,3-dihydroimidazol-2-one, 1-[ 1- {3 -(Aminomethyl)benzyl} -3 -indolyl]-5-(1-methyl-3-indolyl)-1,3-dihydroimidazol-2-one, 5-[1-(3-Amidinothiopropyl)-3-indolyl]-1-(3-indolyl)-1,3-dihydroimidazol-2-one, 1-(1-Ethoxycarbonyl-3-indolyl)-5-(3-naphthyl)-4-methyl-1,3-dihydroimidazole-2-one, A 1,5-Bis-(3-indolyl)-4-methyl-1,3-dihydroimidazol-2-one, --.

Column 20,
Line 23, delete "dibydroimidazol" and insert -- dihydroimidazol --.
Line 29, delete "1-metlhyl-" and insert -- 1-methyl --.

Signed and Sealed this

First Day of February, 2005

JON W. DUDAS
*Director of the United States Patent and Trademark Office*